United States Patent
Szabo et al.

(10) Patent No.: US 8,201,439 B2
(45) Date of Patent: Jun. 19, 2012

(54) MATERIAL WETTABILITY CHARACTERIZATION AND CHEMICAL ADDITIVE EVALUATION

(75) Inventors: Geza Horvath Szabo, Edmonton (CA); Dmitry Eskin, Edmonton (CA); Wael Abdallah, Edmonton (CA); Paul Swenson, Sherwood Park (CA)

(73) Assignee: Schlumberger Technology Corporation, Sugar Land, TX (US)

( * ) Notice: Subject to any disclaimer, the term of this patent is extended or adjusted under 35 U.S.C. 154(b) by 407 days.

(21) Appl. No.: 12/610,578

(22) Filed: Nov. 2, 2009

(65) Prior Publication Data

US 2011/0106456 A1     May 5, 2011

(51) Int. Cl.
*G01N 13/00* (2006.01)
(52) U.S. Cl. ..................... 73/64.48; 73/64.55
(58) Field of Classification Search ............... 73/53.05, 73/61.41, 61.44, 64.55, 152.06, 152.08
See application file for complete search history.

(56) References Cited

U.S. PATENT DOCUMENTS

| | | | | |
|---|---|---|---|---|
| 2,995,027 A * | 8/1961 | Bernard et al. | ................. | 73/38 |
| 3,643,738 A * | 2/1972 | Dreher et al. | ................. | 166/252.1 |
| 4,790,180 A * | 12/1988 | Sinnokrot | ................. | 73/152.07 |
| 5,069,065 A * | 12/1991 | Sprunt et al. | ................. | 73/152.09 |
| 5,162,733 A * | 11/1992 | Baldwin | ................. | 324/307 |
| 5,663,499 A * | 9/1997 | Semmelbeck et al. | ................. | 73/152.06 |
| 5,679,885 A * | 10/1997 | Lenormand et al. | ................. | 73/38 |
| 6,272,906 B1 * | 8/2001 | Fleury et al. | ................. | 73/64.55 |
| 6,765,380 B2 * | 7/2004 | Freedman et al. | ................. | 324/303 |
| 7,397,240 B2 * | 7/2008 | Fleury et al. | ................. | 324/303 |
| 7,532,983 B2 * | 5/2009 | Montaron | ................. | 702/7 |
| 8,076,933 B2 * | 12/2011 | Freedman | ................. | 324/303 |
| 2004/0000905 A1 * | 1/2004 | Freedman et al. | ................. | 324/303 |
| 2004/0168506 A1 * | 9/2004 | Knebel et al. | ................. | 73/61.44 |
| 2004/0255650 A1 * | 12/2004 | Moudgil et al. | ................. | 73/64.55 |
| 2009/0011222 A1 * | 1/2009 | Xiu et al. | ................. | 428/323 |

FOREIGN PATENT DOCUMENTS

JP         2010054312 A  *  3/2010

(Continued)

OTHER PUBLICATIONS

Princen, "The Equilibrium Shape of Interfaces, Drops, and Bubbles, Rigid and Deformable Particles at Interfaces," Surface and Colloid Science vol. 2, Ed. Egon Matijević, New York: John Wiley & Sons, 1969: pp. 1-84.

(Continued)

*Primary Examiner* — David Rogers
(74) *Attorney, Agent, or Firm* — William L. Wang; Wayne J. Kanak

(57) ABSTRACT

Methods and related systems are described for determining a property of a solid material relating to wettability, and for evaluating chemical additives. A solid particle is positioned at an interface between a lighter fluid phase, such as oil, and a denser fluid phase, such as water. An external force is applied, preferably with a centrifuge, so as to urge the solid particle into the denser fluid phase. An observation is made as to whether the particles has passed through the denser fluid phase, and based on the observation the contact angle is calculated. The calculation is also based on the densities of each fluid phase, of the solid material, the amount of the external force applied, size of the solid material, and interfacial tension between the two phases. The calculation also preferably accounts for two curvatures representing the interface between the first phase and the second phase as deformed by the solid material.

46 Claims, 17 Drawing Sheets

FOREIGN PATENT DOCUMENTS

| | | | |
|---|---|---|---|
| RU | 1777048 A1 | * | 11/1992 |
| SU | 761884 B | * | 9/1980 |
| SU | 1223086 A | * | 4/1986 |

OTHER PUBLICATIONS

Rapacchietta et al., "Force and Free-Energy Analyses of Small Particles at Fluid Interfaces: II Spheres," Jounal of Colloid and Interface Science, May 1977, vol. 59(3): pp. 555-567.

Nutt, "Froth Flotation: The Adhesion of Solid Particles to Flat Interfaces and Bubbles," Chemical Engineering Science, 1960, vol. 12: pp, 133-141.

Treiber et al., "A Laboratory Evaluation of the Wettability of Fifty Oil-Producing Reservoirs," Society of Petroleum Engineers Journal Transactions; Dec. 1972, vol. 253: pp. 531-540.

Amott et al., "Observations Relating to the Wettability of Porous Rock," Petroleum Transactions, AIME, 1959, vol. 216; pp. 156-162.

Tiab et al., "Chapter 6: Wettability," Petrophysics Second Edition: Theory and Practice of Measuring Reservoir Rock and Fluid Transport Properties, New York: Gulf Professional Publishing, 2004: pp. 360-382.

\* cited by examiner

| Surfactant | Run | G Force | Interfacial Tension | $\beta_{Calculated}$ | $\beta_{Corrected}$ | $\beta_{Measured}$ |
|---|---|---|---|---|---|---|
| No Surfactant | 1 | 65.58 | 51.04 | 103.83 | 110.00 | 131.31±3.71 |
|  | 2 | 65.58 | 51.04 | 103.83 | 110.00 |  |
|  | 3 | 67.51 | 51.04 | 105.74 | 110.50 |  |
| SDS | 1 | 15.91 | 9.89 | 120.54 | 129.50 | 139.02±4.09 |
| 1xCMC | 2 | 18.81 | 9.89 | 137.40 | 154.00 |  |
|  | 3 | 13.98 | 9.89 | 110.37 | 116.50 |  |
| Triton X-100 | 1 | 11.09 | 9.32 | 99.04 | 103.50 | 113.31±3.86 |
| 1xCMC | 2 | 12.06 | 9.32 | 104.26 | 109.50 |  |
|  | 3 | 9.64 | 9.32 | 91.16 | 94.50 |  |

MATERIAL WETTABILITY CHARACTERIZATION AND CHEMICAL ADDITIVE EVALUATION

BACKGROUND

1. Field of the Invention

This patent specification relates to apparatuses and methods for wettability characterization of solid material. More particularly, the patent specification relates to apparatuses and methods for characterizing wettability of solid material by positioning the material at the interface between two fluids and applying an external force, such as with a centrifuge.

2. Description of Related Art

Wettability is one of the major parameters, which can be used to characterize oil recovery efficiency. If a porous rock is oil wet, which is the case when the contact angle of an oil/water system on the surface of the solid approaches 180°, then only a small fraction of oil is recoverable. This can be observed, for example, in carbonate reservoirs. In a case of water wet rock, which is the case when the contact angle of an oil/water system on the surface of the solid approaches 0°, the oil recovery efficiency is much higher. Contact angle ranges have been introduced to characterize the water-wet, intermediate wet, and oil-wet characteristics of reservoir rocks. See, L. E. Treiber, D. L. Archer and W. W. Owens, *Laboratory Evaluation of the Wettability of Fifty Oil-Producing Reservoirs*, Soc Pet Eng J 12, 531 (1972). It is important to evaluate the contact angle to characterize oil recoverability. Contact angle is most often measured directly by optical means although alternative non-optical techniques are also described in the art. The optical contact angle measuring technique has the following inherent problems: (i) a geometrically and energetically homogenous macroscopic solid surface is needed; (ii) the advancing and retreating contact angles should be measured independently and the equilibrium contact angle needs to be calculated based on some theoretical approach; (iii) the contact angle measurements need some equilibration time, hence these measurements are time consuming; (iv) sophisticated image capturing and analyzing software is necessary; and (v) one of the phases should be optically clear. One also has to realize that only one additive with a specified concentration could be tested with the same instrument at a time because of the equilibration time and complexity of measurements. Consequently it takes a long time to screen the effect of added chemicals as a function of chemistry and concentration on the contact angle. Therefore it would be beneficial to develop a screening methodology, which would request less sophisticated experimental apparatus and would make possible parallel screening of a large number of samples.

Currently in the oilfield industry, the wettability is preferably characterized by the US Bureau of Mines (USBM) Wettability Index based on the work done to introduce each phase into a core at residual saturation for that phase. Starting with a core saturated with oil at irreducible water saturation, water is allowed to imbibe spontaneously into the core followed by forced imbibition of water until residual oil saturation is attained. Next oil is allowed to imbibe spontaneously into the core followed by forced imbibition of oil till the core reverts to irreducible water saturation. Throughout the process the capillary pressure is plotted versus saturation. The area under the curve between the capillary pressure line and the x-axis represents the work done to force the given phase into the core. The USBM Wettability Index is the difference of the logarithm of the area above the Pc=0 axis and the area below the Pc=0 axis. The centrifugation of a macroscopic core sample could be used to establish and calculate the equilibrium capillary pressures. The details of this procedure were published in: D. Tiab and E. C. Dionaldson, *Petrophysics*, Gulf Publishing Co., (2004).

The wettability index characterizes wettability but does not provide the quantitative information about a wetting system. The Amott wettability index, $I_A$, is also used to characterize wettability of reservoir rocks. Sett, E. Amott, *Observations relating to the wettability of porous rock*, Trans. AIME 216, 156 (1959). It is based on spontaneous imbibition and forced displacement of water and oil. It is defined with the following formula:

$$I_A = \frac{V_{OSP}}{V_{OT}} - \frac{V_{WSP}}{V_{WT}}$$

Where $V_{WSP}$ is the volume of water displaced by spontaneous imbibition of oil; $V_{WT}$ is the total volume of water displaced by the forced imbibition of oil; $V_{OSP}$ is the volume of oil displaced by spontaneous imbibition of water; $V_{OT}$ is the total volume of oil displaced by the forced imbibition of water.

Applying an external force from a centrifuge to a particle at an air-water interface has been investigated. See, C. W. Nutt, *Froth Flotation: The adhesion of solid particles to flat interfaces and bubbles*, Chem. Engineering. Sci. Vol. 12, pp 133 to 141 (1960), discusses an investigation of experiments and derived equations for the force and work required to detach a particle from an air-water interface as a function of solid and liquid densities, the surface tension and the angle of contact. However, in this paper only air-water systems were investigated so it was possible to neglect the density of air, which led to simplified mathematical formulations. Also, the curvature of the meniscus was described by only single curvature, and therefore only one curvature was used in the Laplace Equation. The rotation speed was calculated and then compared with their experimental results. Finally, there is no discussion of attempting to determine wettability.

BRIEF SUMMARY

According to embodiments, method for determining a property of a solid material relating to wettability is provided. The method includes positioning a solid material at an interface between a first fluid phase and a second fluid phase, the second fluid phase being denser than the first fluid phase. An external force is applied to the solid material so as to urge the solid material towards the second fluid phase. A determination is made whether the solid material passes through the second fluid phase due to the external force. A parameter of the solid material related to wettability (such as the contact angle) is calculated based on whether the solid material has passed through the second fluid phase. The calculation of the contact angle is preferably based on the measured densities of both the first and second phases, the density of the solid material, the interfacial tension between the phases, the size of the solid material and the minimum external force applied to particle to transport it through the interface. In the following discussion the size of the solid material is represented by the radius of an equivalent sphere. The calculations preferably account for two curvatures representing the interface between the first phase and the second phase as deformed by the solid material. A centrifuge preferably provides the external force. Gravitational force could also be used as external force. Examples of the first phase include a gas, or an organic solution such as oil. Examples of the second phase include an organic solution or an aqueous solution.

According to other embodiments a method for evaluating a chemical additive is provided. The method includes positioning the solid, applying the external force and determining if the solid passes through the second phase as described above. The method also includes evaluating a chemical additive contained in either of the fluid phases based at least in part on whether the solid material passes through the interface between the phases. The evaluation method can be performed as a batch process, by positioning many pieces of the solid material in many containers containing the first and second phases. The external force is applied simultaneously, preferably using a centrifuge, and a determination is made for each of the containers whether one or more of the pieces of the solid material passes through the interface due to the external force. Different amounts or different compositions of chemical additives can be added to each of the containers, thereby facilitating the evaluation.

According to other embodiments, systems for determining a property of a solid material relating to wettability, and for evaluating a chemical additive are also provided.

Further features and advantages of the invention will become more readily apparent from the following detailed description when taken in conjunction with the accompanying drawings.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 19 is a table showing experimental results, according to some embodiments.

Figure 1:
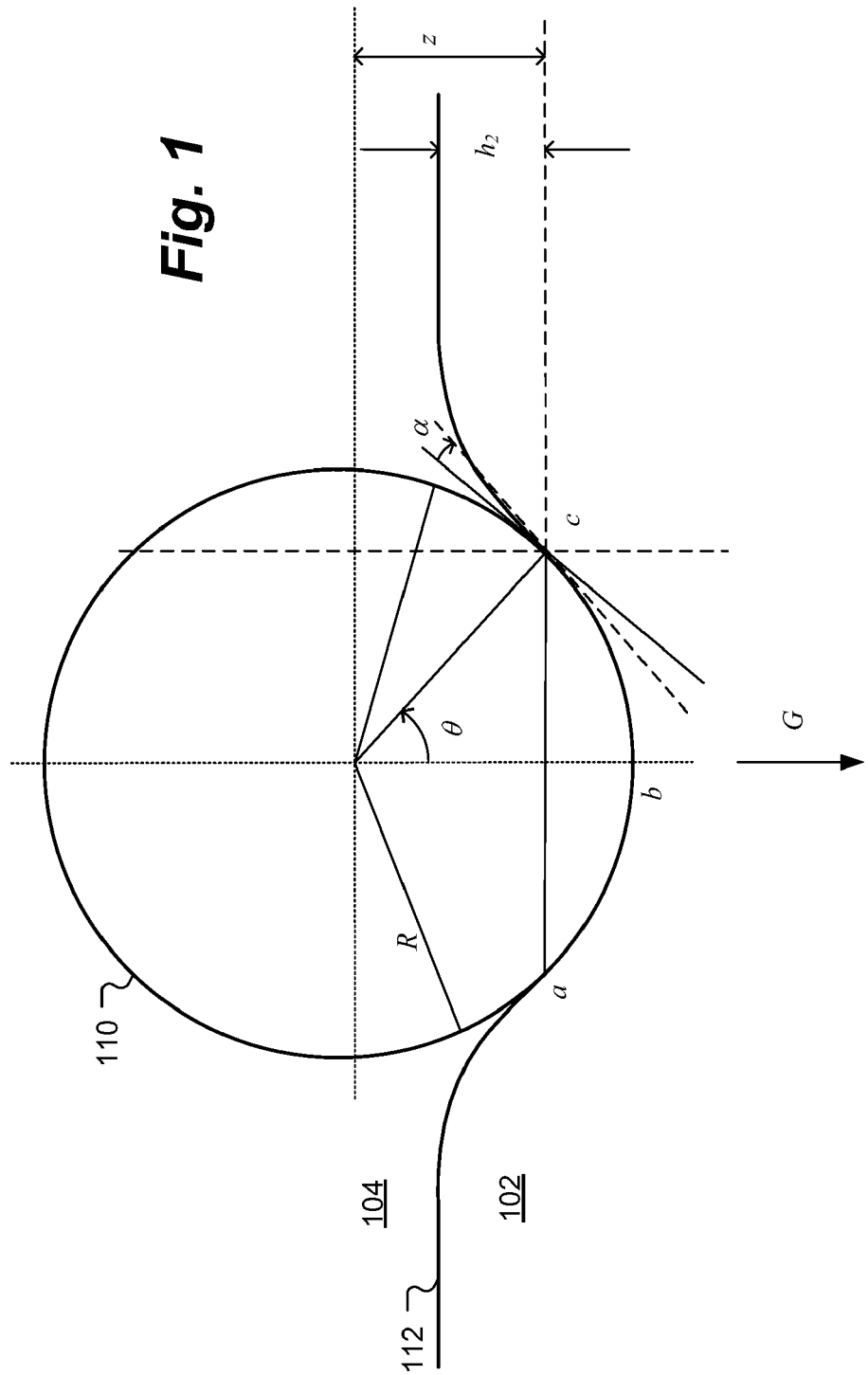
FIG. 1 is a diagram showing the calculation for a spherical particle transported through a water-oil interface, according to some embodiments.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the scope of the invention as defined by the appended claims.

DETAILED DESCRIPTION

Illustrative embodiments of the invention are described below. In the interest of clarity, not all features of an actual implementation are described in this specification. It will be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure. Further, like reference numbers and designations in the various drawings indicated like elements.

Consider a spherical particle, a surface of which is oil wet, located in oil in the vicinity of an oil-water interface. To transport this particle from the oil to the water it is necessary to overcome the capillary force acting on the particle during the crossing of the interface. According to some embodiments, a centrifuge is used to create an external force to displace particle from the oil to the water. The centrifugal acceleration can be easily controlled by the centrifuge rotation speed. The capillary force can be accurately calculated for a spherical particle if the following parameters are known: the particle size, the densities of the particle, the density of the oil, the density of the water, the oil-water interfacial tension, and the contact angle. Thus, if the minimum rotation speed at which the particle is able to penetrate through the oil-water interface is known the contact angle can be calculated if the all other system parameters, mentioned above except the contact angle, are known.

A discussion of modeling of particle transport through the oil-water will now be provided. Both an accurate numerical and an approximate analytical solutions are considered. An analysis of particle transport sensitivity to process parameters is fulfilled.

Initially carbonate particles are oil wet. Thus, if the system includes of the two layers (water and oil) some external mass force should be applied to a particle to transport it from oil to water. This external force should exceed the force caused by a capillary effect. FIG. 1 is a diagram showing the calculation for a spherical particle transported through a water-oil interface, according to some embodiments. Particle 100 is shown positioned at an interface 112 between an upper fluid phase 104 and a lower fluid phase 102. The upper phase 104 is less dense than the lower phase 102, and according to many embodiments the upper phase 104 is a type of oil and the lower phase 102 is a type of water. According to some embodiments, one or both phases contain additives to be evaluated. R is the radius of particle 110; $h_2$ is the meniscus height; $\beta=\pi-\alpha$ is the contact angle in agreement with the convention according to which the contact angle should be measured in the denser phase, which is usually the water phase; $\theta$ is the angle determining the position of the upper phase, lower phase, and particle contact circumference; and G represents the external mass force applied. It is convenient to control the external mass force in a centrifuge. A number of test tubes filled half with oil and half with water on top are placed along a centrifuge circumference. Carbonate particles are either preliminary dispersed in oil or they can be dropped into the oil phase on the top. A certain rotation speed is needed to provide a transport of particles of a given size from oil to water. Various chemicals added to different oil samples reduce both the interfacial tension and the contact angle. The bigger number of particles transported through the oil-water interface indicates stronger modification of the interfacial layer by the additive. If the interfacial tension is known, preferably by measurement, the contact angle can be evaluated based on a modeling of particle transport through the interface.

Modeling. There are articles where a problem of particle transport through liquid-liquid interface is considered. For example, see A. V. RAPACCHIETTA AND A. W. NEUMANN, Force and Free-Energy Analyses of Small Particles at Fluid Interfaces, II. Spheres, Journal of Colloid and Interface Science, Vol. 59(3), pp. 55-567 (1977); and PRINCEN, H. M., "Surface and Colloid Science" (Ed. E. Matilevic), Vol. 2, p. I., Interscience, New York (1969). Both of which are incorporated herein by reference. We assume that the particle transport is slow, i.e. the particle acceleration can be neglected. At slow transport it can also be assumed that interfacial tension between the two fluid phases is at equilibrium, and that an equilibrium contact angle on the solid surface is formed. Since our purpose is obtaining data to design a centrifugal device for evaluation of particle wettability, it is important to obtain an accurate solution of this problem. Such a solution can be obtained numerically.

The solution of this problem makes use of the 2 equations: (1) a momentum equation for a sphere; and (2) an equation describing a shape of the water-oil boundary in the sphere vicinity. The momentum equation for a sphere on an oil-water boundary represents a force balance. On the one hand according to the Archimedes law the weight of a sphere can be calculated as:

$$W = [(\rho_s - \rho_w) \cdot V_{abc} + (\rho_s - \rho_o) \cdot V_{abcd} - (\rho_w - \rho_o) \cdot h_2 \cdot ab] \quad (1)$$

where $h_2$ is the meniscus height, V is the volume (see FIG. 1), $\rho_o, \rho_w, \rho_s$, are the densities oil, water and solids respectively.

The first two terms on the right-hand side of Equation (1) determine the weights of the sphere elements immersed in water and oil respectively. The third term determines the weight reduction of the sphere's part immersed in oil due to the displaced water layer of the thickness $h_2$.

The particle weight is equilibrated by the force caused by the solids-oil-water interface colloidal interactions:

$$I = \gamma_{ow} \cdot 2\pi \cdot ab \cdot \sin(\theta-\alpha) \gamma_{ow} = \gamma_{ow} \cdot 2\pi R \sin\theta \cdot \sin(\theta-\alpha) \quad (2)$$

where $\beta=\pi-\alpha$ is the contact angle (see FIG. 1), $\gamma_{ow}$ is the oil-water interfacial energy, $\theta$ is the angle determining the position of the oil-water-solids contact circumference.

The following force balance equation determines the particle behavior at the oil-water interface:

$$F_\Sigma = W - I \quad (3)$$

If $F_\Sigma$ is positive the particle moves towards the external mass force G applied. If $F_\Sigma$ is negative particle cannot penetrate trough the oil-water interface. For practical application of Equation (3) the position of a particle relative to interface should vary for the all possible particle positions: $\theta=[0;\pi]$, (z=[0:2R]).

After routine math treatment the expression for the force $F_\Sigma$ takes the form:

$$F_\Sigma (\rho_s - \rho_o) G \frac{4}{3}\pi R^3 - \qquad (4)$$

$$(\rho_w - \rho_o) G \left[ \pi R^3 \left( \frac{2}{3} - \cos\theta + \frac{\cos^3\theta}{3} \right) + \pi R^2 h_2 \sin^2\theta \right] - \gamma_{ow} \cdot 2\pi \cdot R\sin\theta \cdot \sin(\theta-\alpha)$$

The shape of the oil-water boundary should satisfy the Laplace equation:

$$\Delta p_c = \gamma_{ow} \left( \frac{1}{r_1} + \frac{1}{r_2} \right) \quad (5)$$

where $\Delta p_c$ is the capillary pressure, $r_1, r_2$ are the main curvature radii of the three dimension interface boundary.

Figure 2:
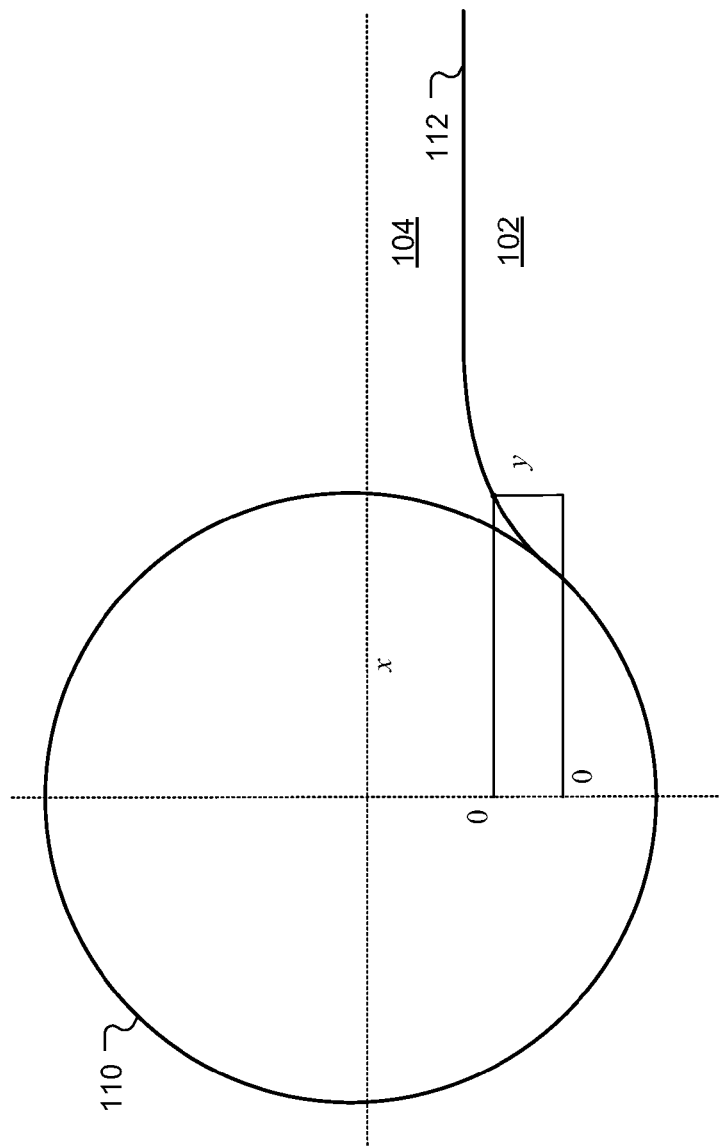
FIG. 2 is a diagram for use in calculations deriving the Laplace equation, according to some embodiments.

FIG. 2 is a diagram for use in calculations deriving the Laplace equation, according to some embodiments. As in FIG. 1, particle 100 is shown positioned at an interface 112 between a less dense upper fluid phase 104 (e.g. oil) and a more dense lower fluid phase 102 (e.g. water). The main curvature radii $r_1$ and $r_2$ can be written through the differential expressions in the coordinate system shown in FIG. 2. The Laplace equation takes the form:

$$\gamma_{ow} \left( \frac{y''}{(y'^2+1)^{\frac{3}{2}}} + \frac{y'}{x(1+y'^2)} \right) = -(\rho_w - \rho_o) g (h_2 - y) \quad (6)$$

The boundary conditions for this equation are:

$$y=0 \; y'=tg(\theta-\alpha) \quad (7)$$

$$y \to h_2 \; y' \to 0 \quad (8)$$

The Laplace equation can be solved analytically if $r_2 \gg r_1$ (similarly to the case of a cylindrically shaped particle). Equation (6) in this case takes the form:

$$\frac{y''}{(y'^2+1)^{\frac{3}{2}}} = \frac{(\rho_w - \rho_o)g}{\gamma_{ow}} (h_2 - y) \quad (9)$$

The analytical solution of this equation (9) is reduced to the simple expression for $h_2$:

$$h_2 = \sqrt{\frac{2}{\xi}(1-\cos(\theta-\alpha))} \quad \text{where} \quad \xi = \frac{(\rho_w - \rho_0)g}{\gamma_{ow}}. \tag{10}$$

Figure 3:
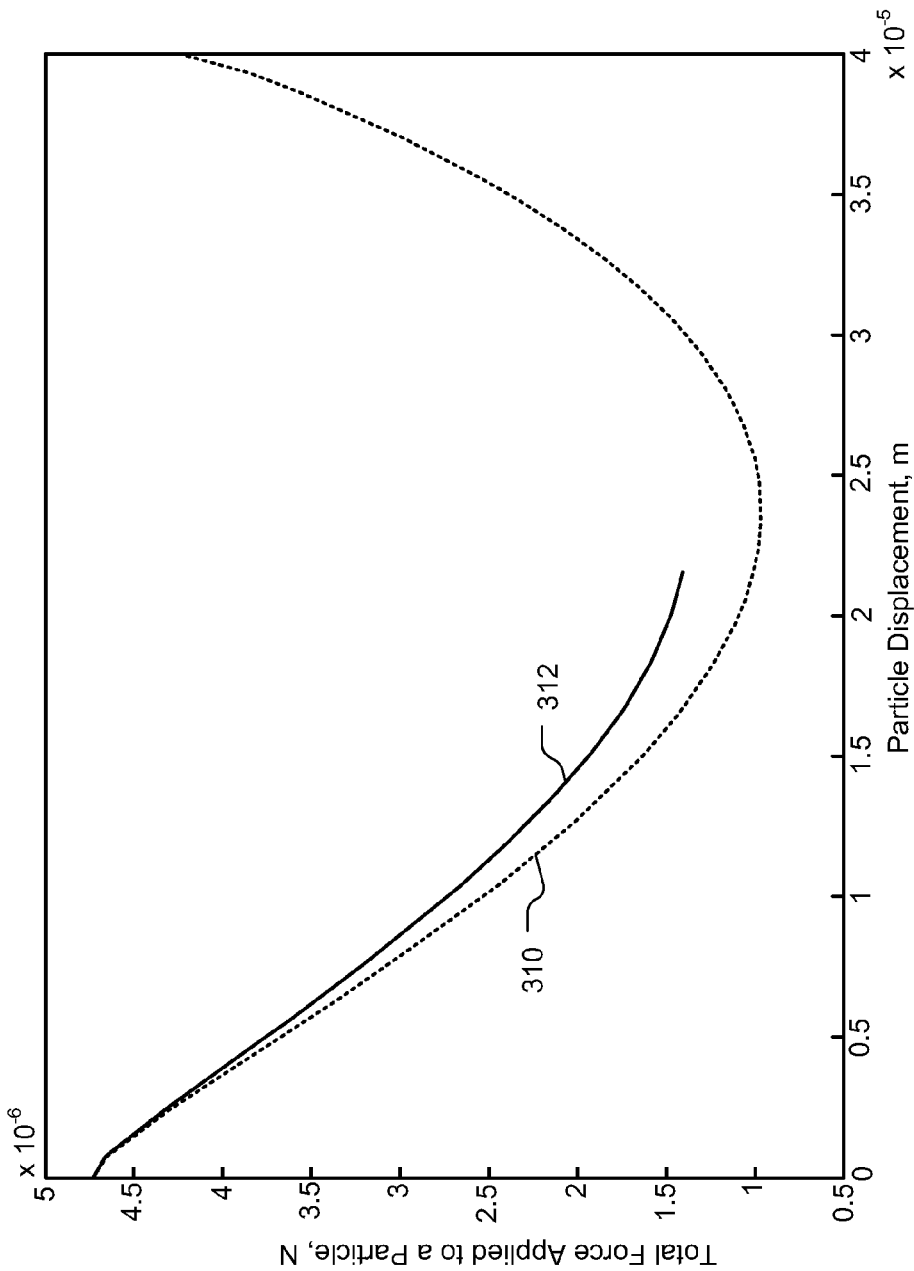
FIG. 3 is a plot of total force applied to a particle vs. particle displacement.
Figure 4:
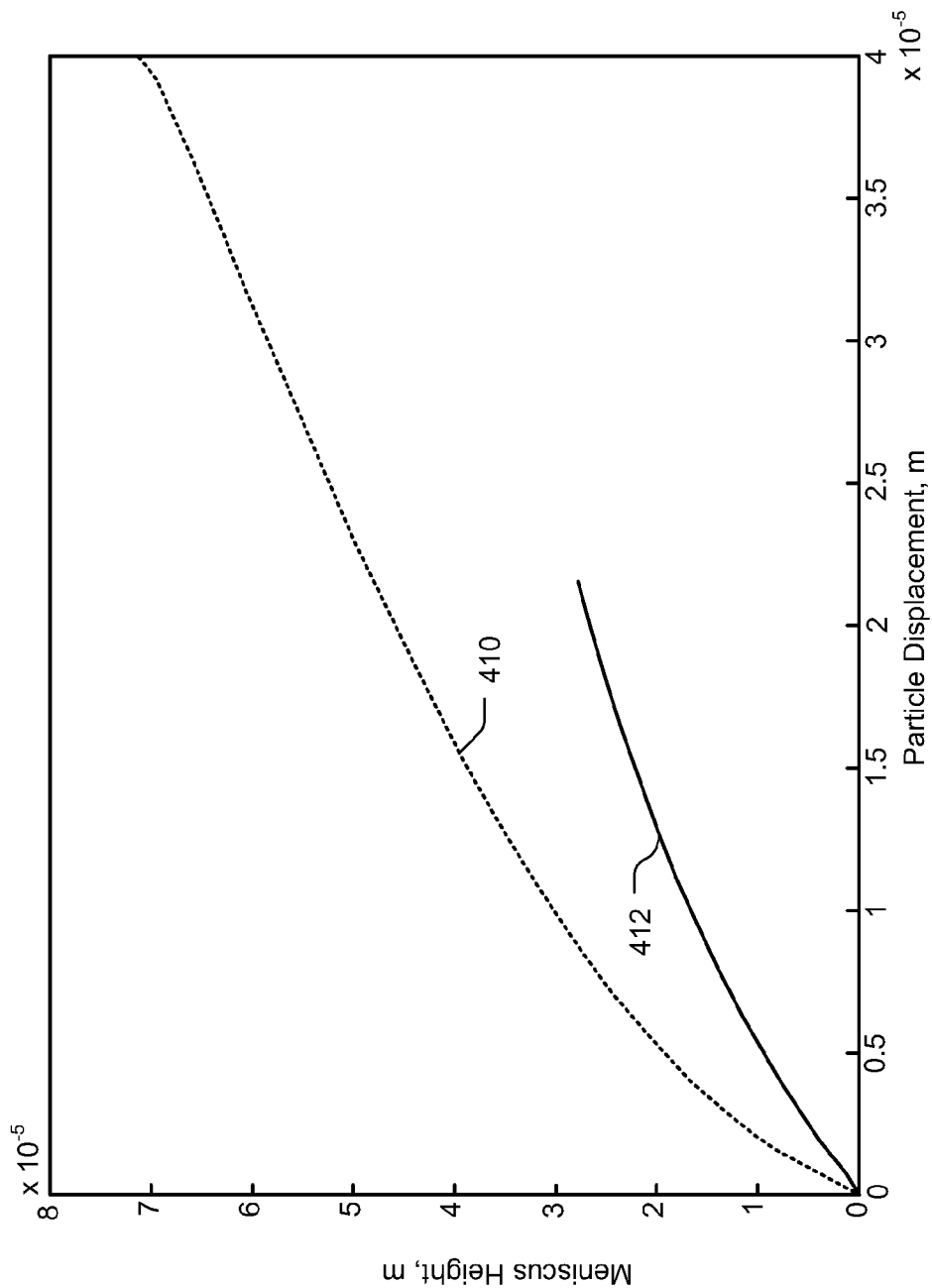
FIG. 4 is a plot of the meniscus height vs. particle displacement.
Figure 5:
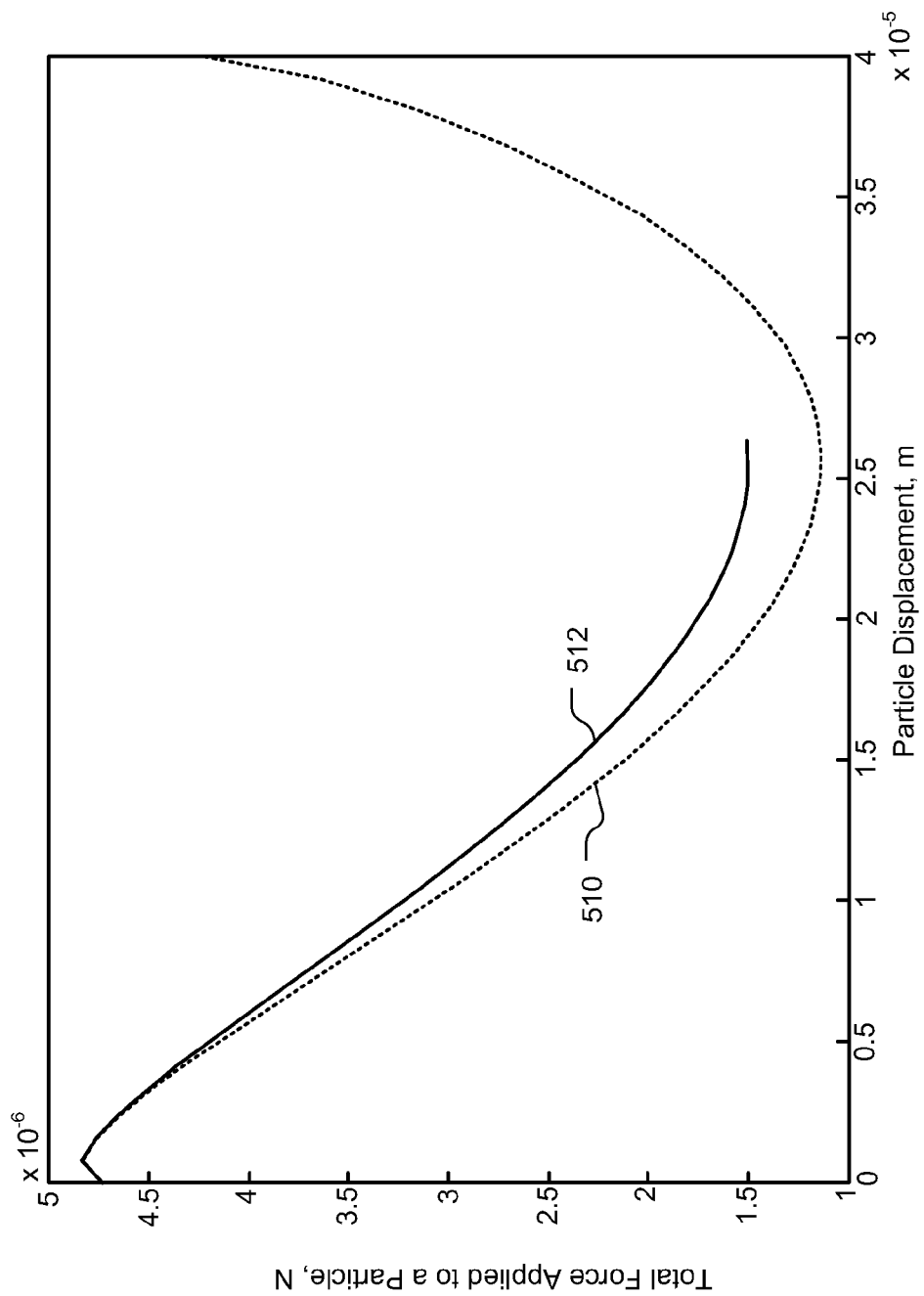
FIG. 5 is a plot of total force applied to a particle vs. particle displacement.
Figure 6:
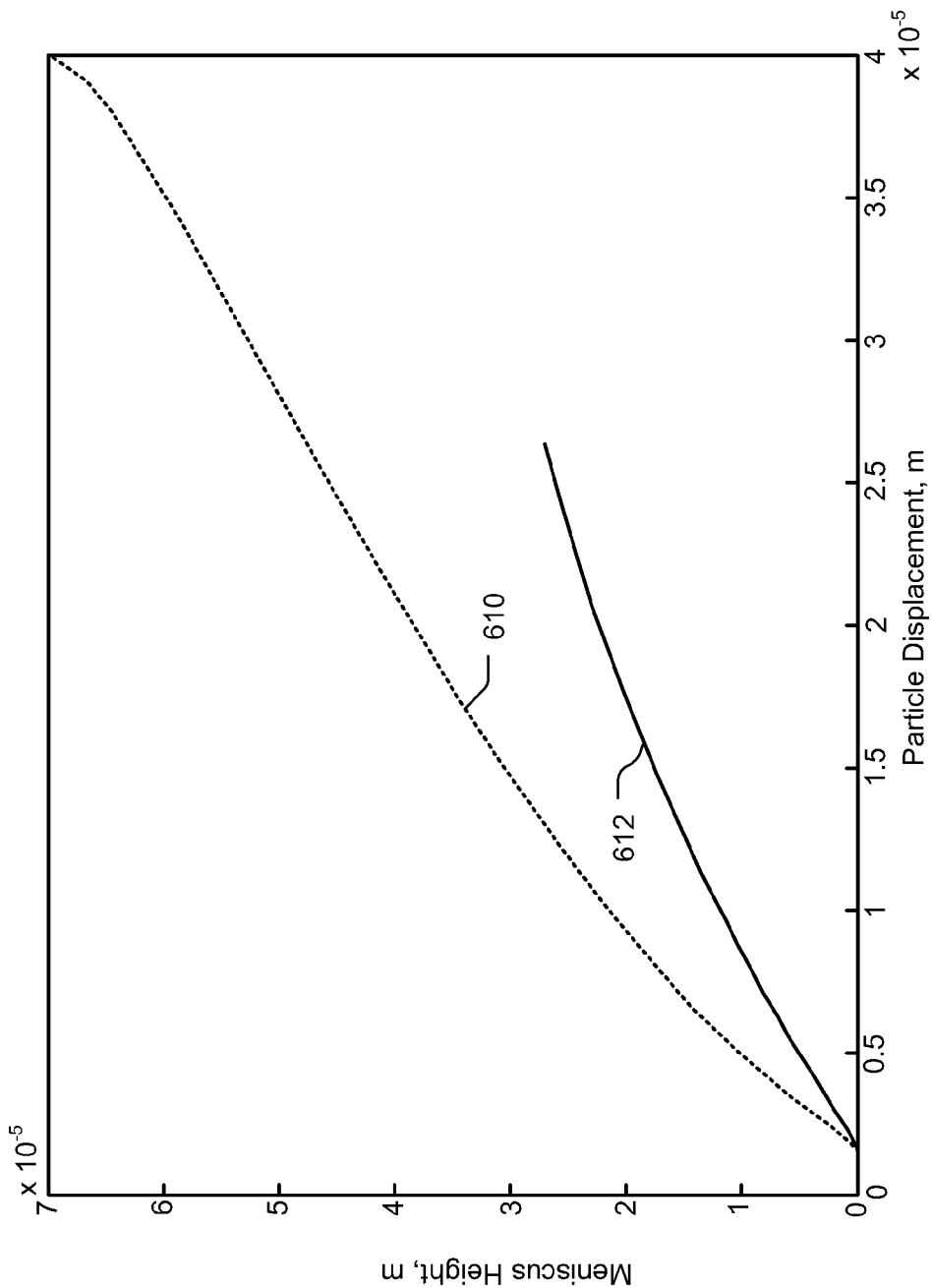
FIG. 6 is a plot of meniscus height vs. particle displacement.
Figure 7:
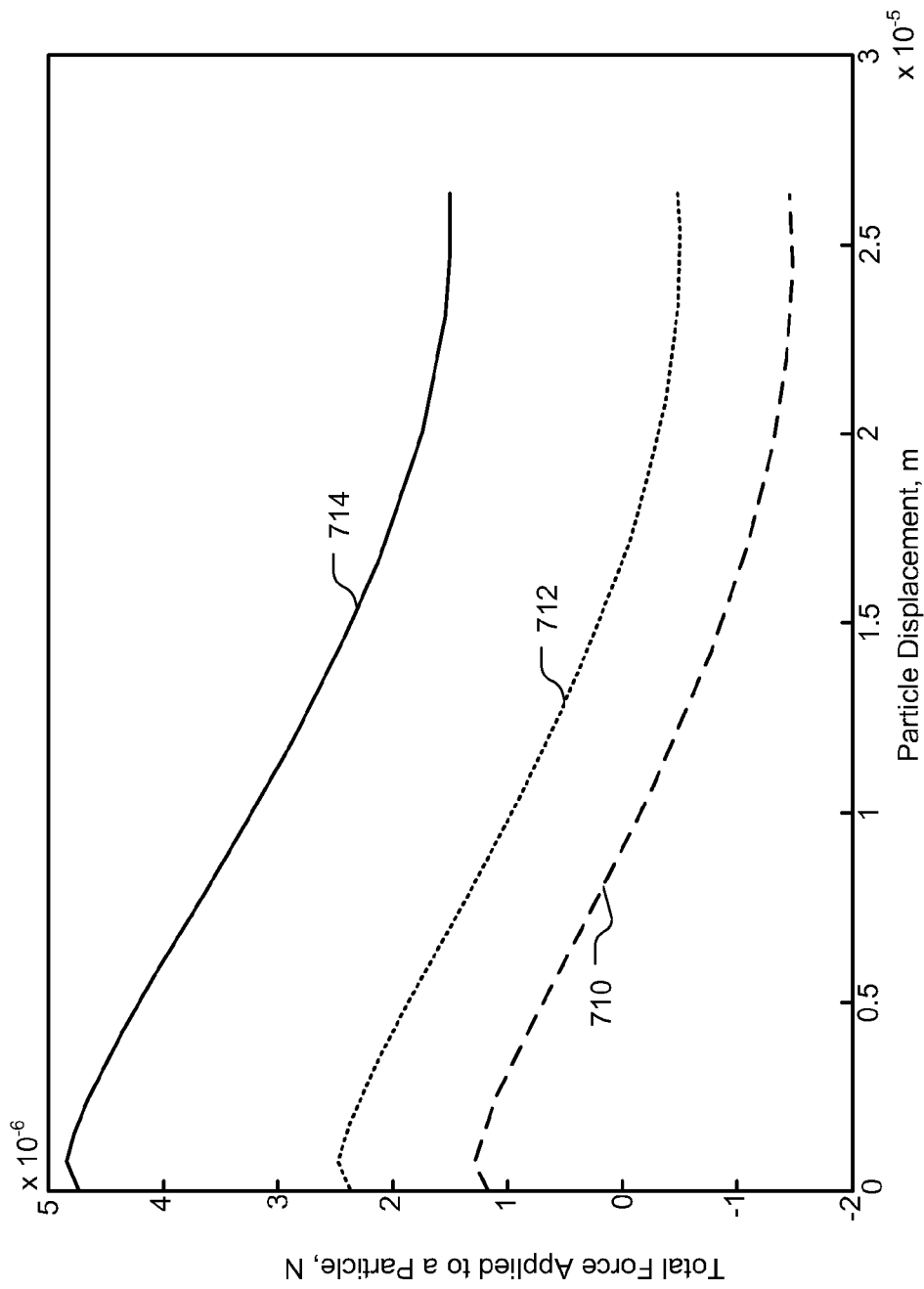
FIG. 7 is a plot of the total force applied to a particle vs. particle displacement for various accelerations.
Figure 8:
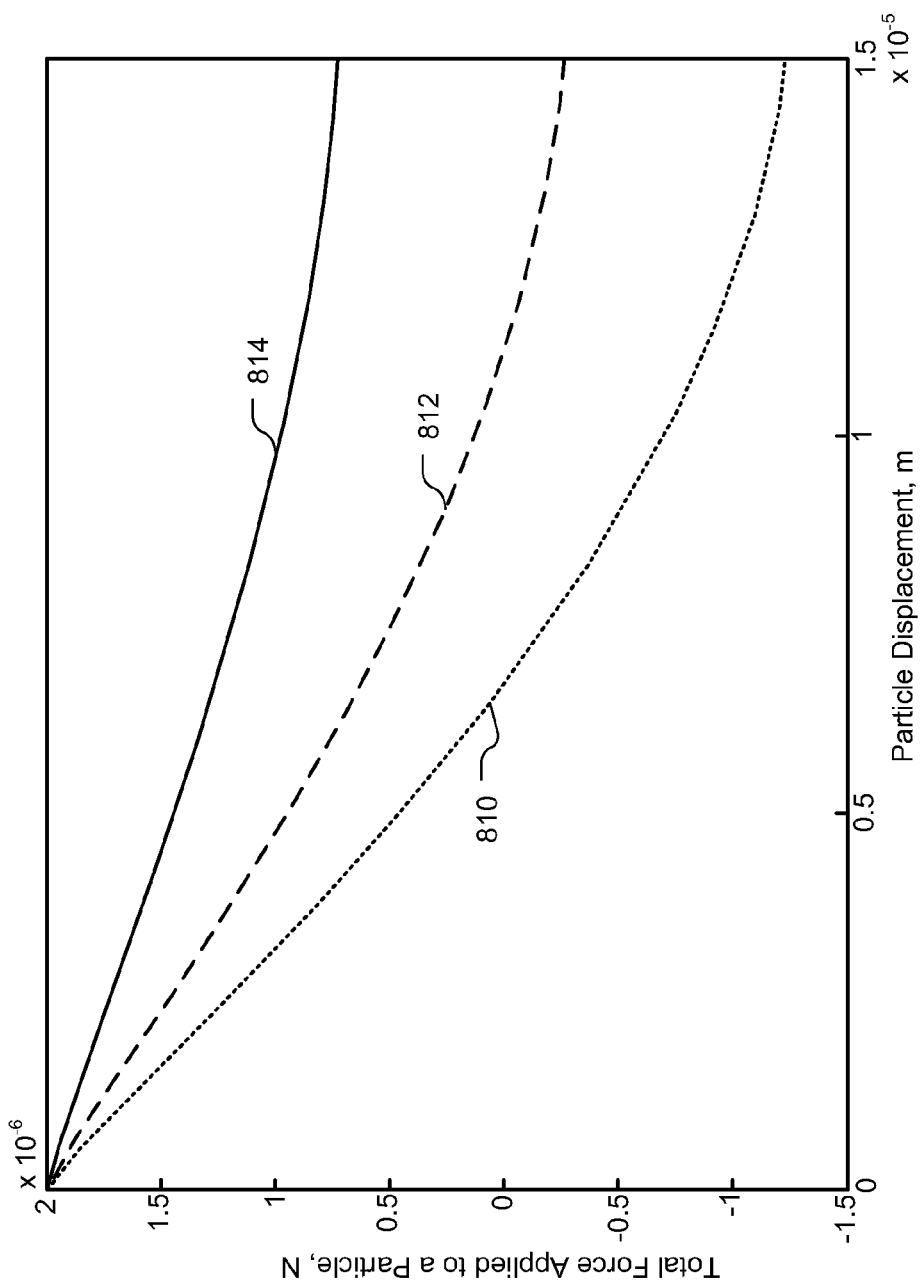
FIG. 8 is a plot of total force applied to a particle vs. particle displacement for various interfacial tension values.
Figure 9:
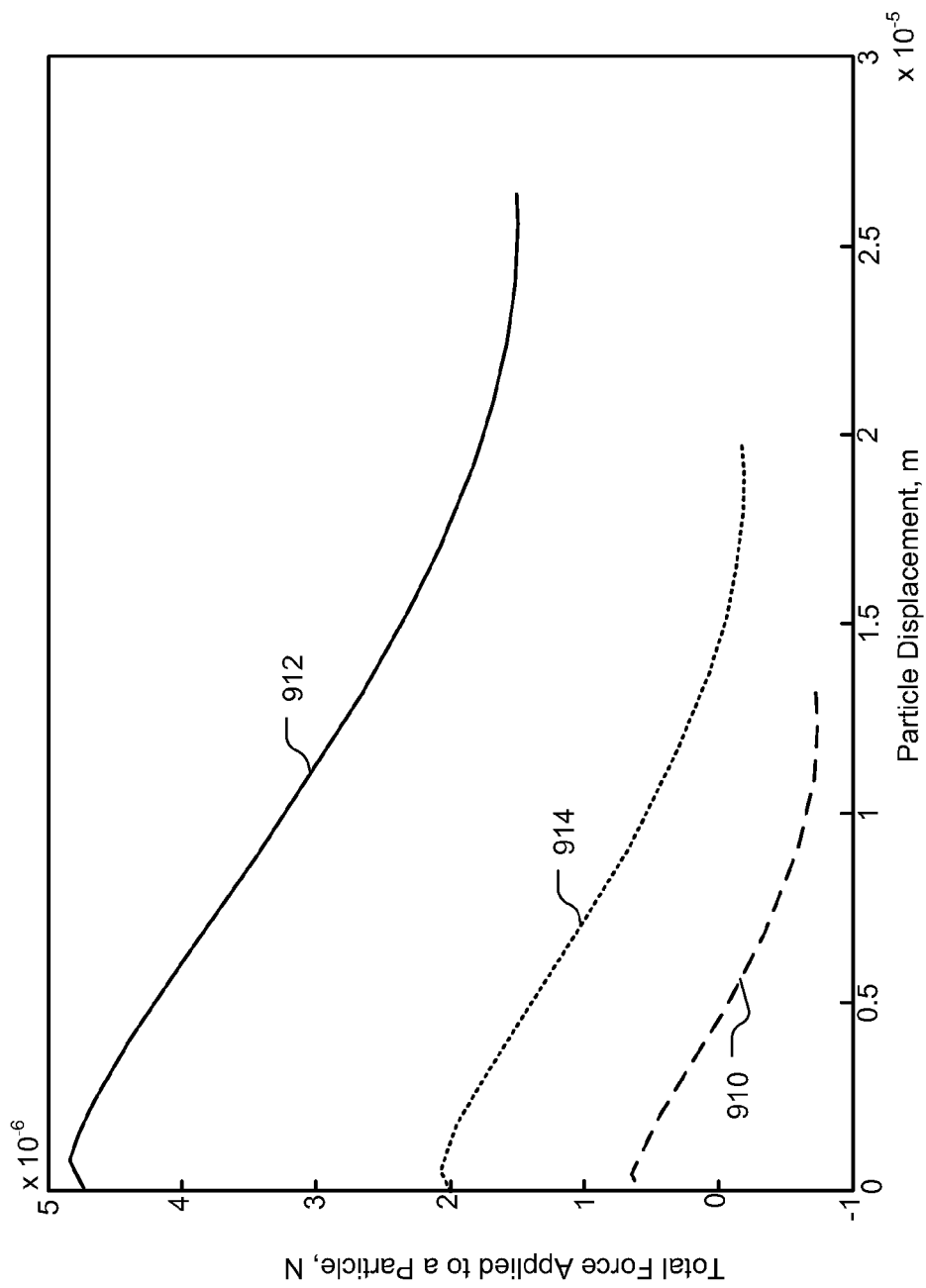
FIG. 9 is a plot of total force applied to a particle vs. particle displacement for various particle diameters.

Calculation Examples. FIGS. 3-9 are plots that illustrate various aspects of the calculation examples described herein. FIG. 3 is a plot of total force applied to a particle vs. particle displacement. Curve 312 is the accurate solution and curve 310 is the approximate solution. The particle diameter is 40 microns, the contact angle is β=100 degrees, the interfacial tension is 20 mN/m, and the centrifugal acceleration is G=8000 g. FIG. 4 is a plot of the meniscus height vs. particle displacement. As in FIG. 3, the particle diameter is 40 microns, the contact angle is 100 degrees, the interfacial tension is 20 mN/m, and the centrifugal acceleration is G=8000 g. Curve 412 is for the accurate calculations and curve 410 is for the approximate calculations. FIG. 5 is a plot of total force applied to a particle vs. particle displacement. The particle diameter is 40 microns, the contact angle is 115 degrees, the interfacial tension is 10 mN/m, and the centrifugal acceleration is G=8000 g. Curve 512 is for the accurate solution and curve 510 is for the approximate solution. FIG. 6 is a plot of meniscus height vs. particle displacement. As in FIG. 5, the particle diameter is 40 microns, the contact angle is 115 degrees, the interfacial tension is 10 mN/m, and the centrifugal acceleration is G=8000 g. Curve 612 is for the accurate solution and curve 610 is for the approximate solution. FIG. 7 is a plot of the total force applied to a particle vs. particle displacement for various accelerations. The particle diameter is 40 microns, the contact angle is 115 degrees and the interfacial tension is 20 mN/m. Curve 710 is for G=2000 g, curve 712 is for G=4000 g, and curve 714 is for G=8000 g. FIG. 8 is a plot of total force applied to a particle vs. particle displacement for various interfacial tension values. The particle diameter is 30 microns, the contact angle is 95 degrees, and the centrifugal acceleration is G=8000 g. Curve 810 is for an interfacial tension of 5 mN/m, curve 812 is for an interfacial tension of 20 mN/m, and curve 814 is for an interfacial tension of 30 mN/m. FIG. 9 is a plot of total force applied to a particle vs. particle displacement for various particle diameters. The interfacial tension is 20 mN/m, the contact angle is 115 degrees, and the centrifugal acceleration is G=8000 g. Curve 910 is for a diameter of 20 microns, curve 912 is for a diameter of 30 microns, and curve 914 is for a diameter of 40 microns.

In FIGS. 3, 5, 6-8 one can see the different dependencies of the total force acting on a particle transported from oil to water as a function of particle displacement z. All these graphs are represent different system conditions. The densities of particle, water and oil were constant for the all calculations:

$$\rho_s = 2600 \frac{kg}{m^3}, \rho_w = 1000 \frac{kg}{m^3}, \rho_o = 800 \frac{kg}{m^3}.$$

The major parameters affecting particle behavior on the interface are the particle size, the interfacial tension and the centrifugal force. The contact angle influences particle transport to smaller extent. To illustrate this in FIGS. 3-6 shows the forces acting on a particle and the meniscus thickness vs. the particle displacement z at the different contact angles (α=100° and 25° respectively). The particle size was d=40 μm, the oil-water interfacial tension was $\gamma_{ow}$=20 mN/m and the centrifugal acceleration was G=8000 g respectively. If the total force is positive for all particle positions the particle can be transported from oil to water. If the calculations indicate the negative force it means that the particle will stack at some position (when the force becomes zero) at the interface. Note that change in the contact angle is usually accompanied with changing the interfacial tension. There is no theory that allows calculating the relation between the interfacial tension and the contact angle.

The calculations performed showed also that the results obtained by the accurate model and the simplified analytical model are not always close to each other. However, the analytical solution can be used as a first approximation for solving the accurate model equations numerically.

In FIGS. 7-9 one can see how the centrifugal acceleration, the oil-water interfacial tension and the particle size affect the total force acting on a particle being displaced from oil to water. It is clear that an increase in the centrifugal acceleration, an increase in the particle size and reduction of the oil-water interfacial tension lead to increasing the total force acting on a particle in the interface vicinity easing the particle transport.

Figure 10:
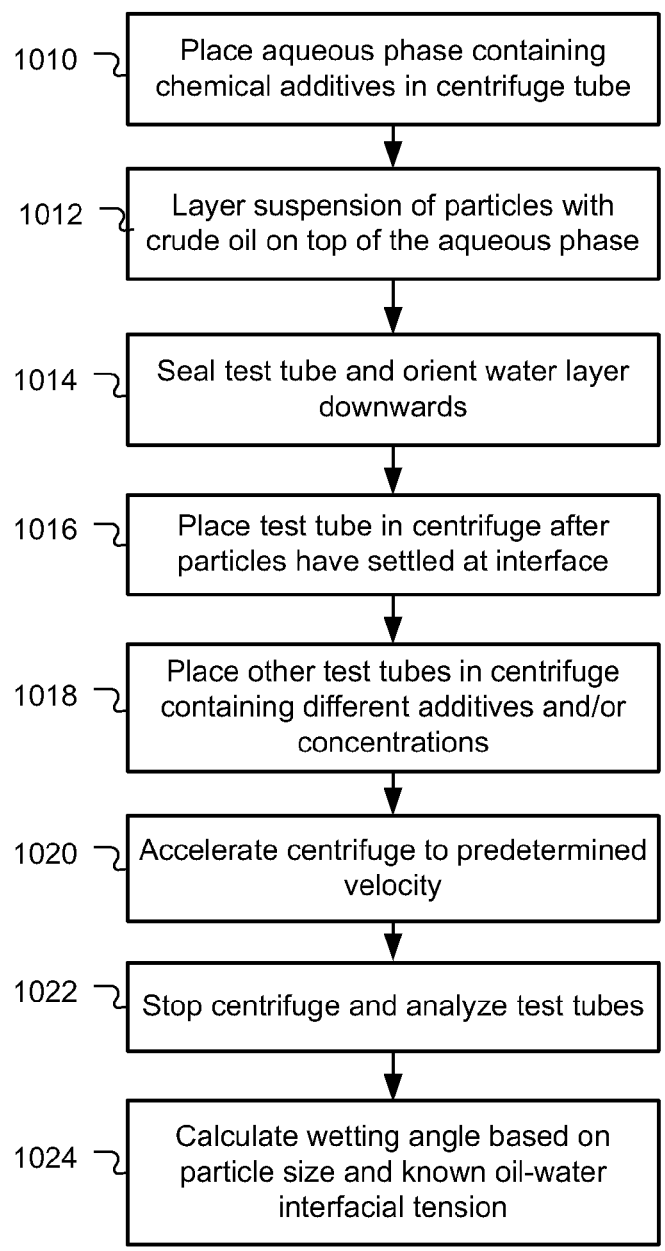
FIG. 10 is a flow chart showing a procedure for contact angle according to some embodiments.

FIG. 10 is a flow chart showing a procedure for contact angle according to some embodiments. Let us consider a small volume sample of oil-wet particles. Particles can be polydispersed or monodispersed (practically, characterized by a narrow particle distribution). The initial particle size or size distribution should be measured. The oil-water interfacial tension should also be measured, for example by using an apparatus as shown and described with respect to FIG. 11. In step 1010, the aqueous phase containing chemical additives is placed into a centrifuge tube. In step 1012, a previously prepared suspension made from the characterizable particles with the crude oil is layered on the top of the water phase. The mean density of the suspension should be lower than the density of the water. If this is not the case then heavy water, $D_2O$, should be used for the preparation of the aqueous phase. In step 1014, the test tube is sealed and oriented "water layer downwards" to provide particle sedimentation to the oil-water interface. A number of particles should be equal or less than the particle number that is necessary to provide a particle monolayer on the oil-water interface under the given geometrical conditions. In step 1016, after accomplishment of particle settling at the interface the test tube should be placed in a centrifuge. In step 1018, multiple test tubes can be installed in a centrifuge. Each test tube may contain different wettability altering additives with different concentrations in the aqueous phase. In step 1020, the centrifuge is accelerated up to a certain velocity and the evaluation of the experimental data should be performed based on the system. For monodisperse system the rotation speed should be slightly lower than that leading to particle penetration through the oil-water interface at the no surfactant case. This rotation speed can be rather accurately calculated for a system of spherical particle if the all system parameters are known. A contact angle of the "no surfactant" system can be evaluated on the basis of some experimental data at disposal or measured by any technique available. For a polydispersed system the rotation speed should be smallest providing penetration of a mean diameter particle through the oil-water interface. In step 1022, after a short time of centrifuge operation, it is stopped and the test tubes are analyzed. The greater the fraction of particles that penetrated through the oil-water interface, the stronger the wettability of a particle surface was modified towards a water wet system. The suggested method allows also an accurate determination of the contact angle for a polydispersed particle system. In step 1026, after finishing a centrifugation procedure the distribution of particles in a section filled with water has to be accurately measured. The equilibrium between the centrifugal and capillary forces, applied to a particle on the oil-water interface, corresponds to the smallest particle. Then at the known oil-water interfacial tension the contact angle can be calculated. Note that the particle sample is preferably small enough so particles could not be located close to each other to exclude particle-particle interaction. According to an alternative embodiment to the above described procedure, a single particle can also be placed in the centrifuge tube instead of many particles or suspensions. In this simplified case the size of the particle can be exactly measured and the contact angle can be determined precisely.

As used herein, the terms "contact angle" and "wetting angle" are interchangeable. Although the term "contact angle" is mainly used herein, it also refers to the wetting angle. The contact angle itself characterizes wettability. The capillary pressure is useful when the fluid intake (either spontaneous or forced) is considered in porous media. This pressure can be calculated for a given capillary radius and for a given contact angle as follows: $\Delta P_c = (2\gamma_{ow} \cos \beta / r$, where $P_c$ stands for capillary pressure, $\gamma_{ow}$ stands for interfacial tension between the oil and water, $\beta$ stands for the contact angle of the liquid against the capillary through which it rises, and r stands for the effective radius of the capillary.

According to some embodiments, for a quick comparative screening of chemical additives the knowledge of the particle size distribution is not needed. In this case the centrifugal force fields at which the breakthrough is observed are to be compared.

According to some embodiments a single particle can also be placed in the centrifuge tube instead of many particles or suspensions. In this simplified case the size of the particle can be exactly known and the contact angle can be determined precisely.

Figure 11:
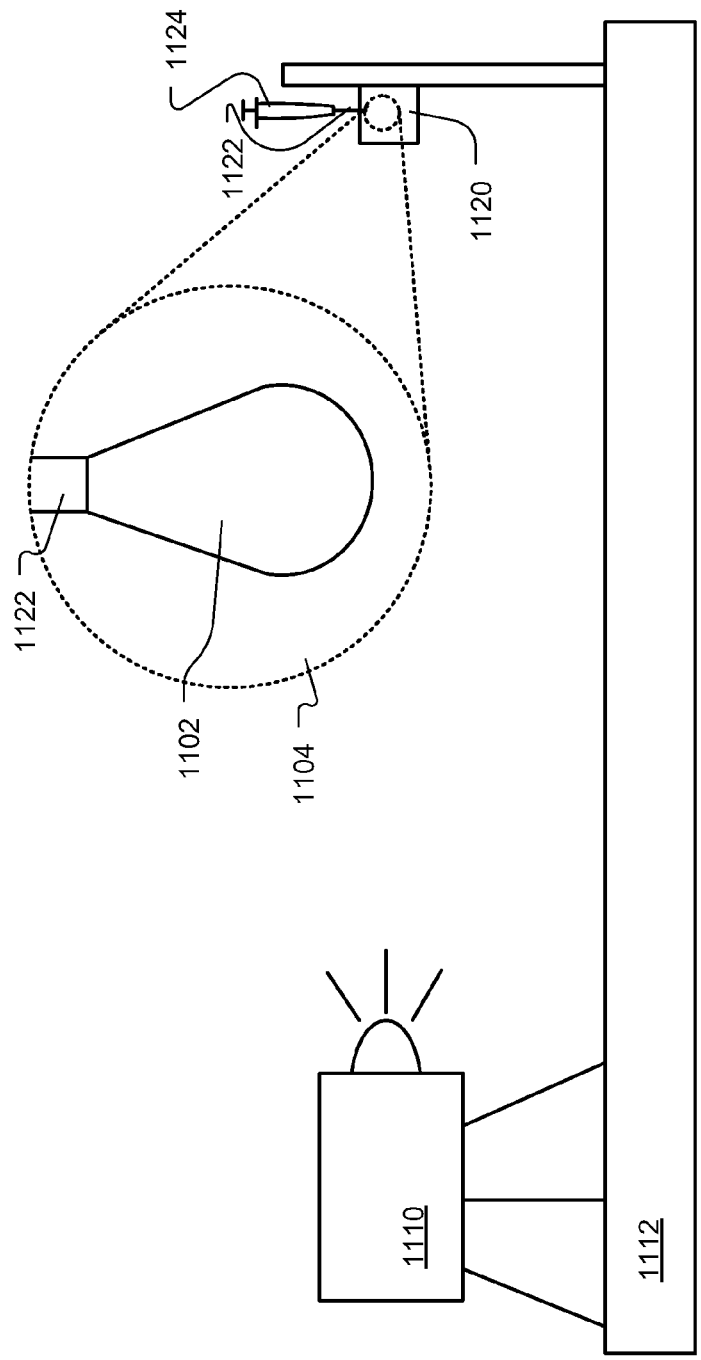
FIG. 11 is a schematic of an interfacial tension measuring apparatus, according to some embodiments.

FIG. 11 is a schematic of an interfacial tension measuring apparatus, according to some embodiments. A cell 1120 is filled with the lighter liquid phase 1104, which in many embodiments is a type of oil. A syringe 1124 is filled with the heavier liquid phase, which in many embodiments is a type of water. The heavier liquid enters the cell via a needle 1122 and forms a drop 1102. The drop 1102 is analyzed using a camera 1110. The camera 1110, cell 1120 and syringe 1124 are all supported by a vibration free base 1112. From the geometry of the drop 1102, the interfacial tension $\gamma_{ow}$ can be measured using a drop shape method as is known in the art.

Figure 12:
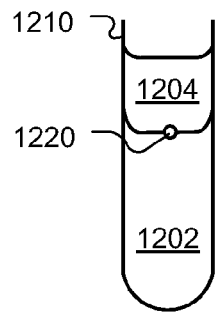
FIG. 12 is a schematic of centrifuge tube in which the particle is situated on the oil-water interface prior to centrifugation, according to some embodiments.

FIG. 12 is a schematic of centrifuge tube in which the particle is situated on the oil-water interface prior to centrifugation, according to some embodiments. Test tube 1210 contains a heavier liquid phase 1202, such as a type of water, and a lighter liquid phase 1204, such as type of oil. The particle 1220 is situated at the interface of the two phases 1202 and 1204.

Figure 13:
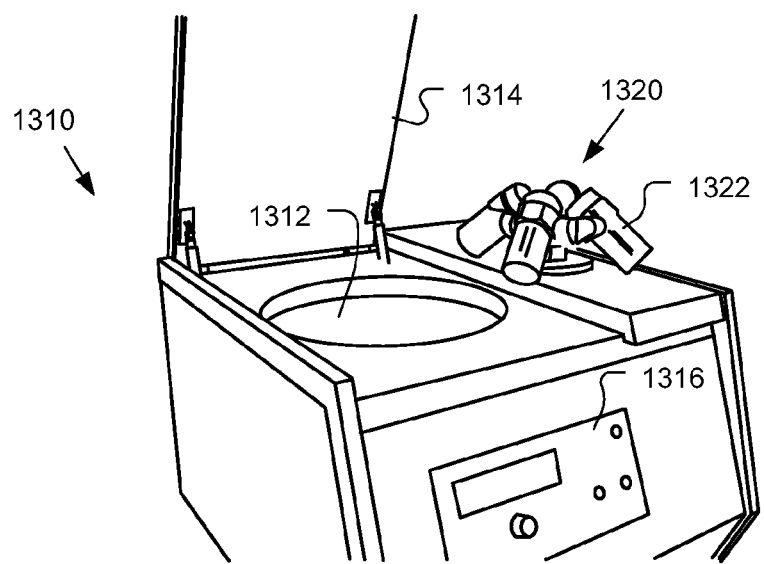
FIG. 13 depicts a bench-top centrifuge system with a rotor, according to some embodiments.

FIG. 13 depicts a bench-top centrifuge system with a rotor, according to some embodiments. Centrifuge 1310 includes a compartment 1312, which accepts a swing-out type centrifuge rotor 1320, and lid 1314. The rotor 1320 includes a number of test tube holders 1322 and each hold a number of test tubes.

Figure 14:
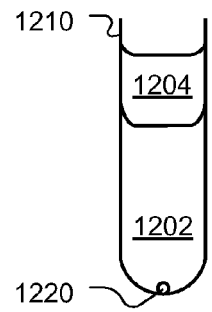
FIG. 14 is a schematic of centrifuge tube in which the particle is situated on the bottom after centrifugation, according to some embodiments.

FIG. 14 is a schematic of centrifuge tube in which the particle is situated on the bottom after centrifugation, according to some embodiments. As in FIG. 12, the test tube 1210 contains a heavier liquid phase 1202, such as a type of water, and a lighter liquid phase 1204, such as type of oil. The particle 1220 is shown at the bottom of the test tube 1210 which indicates that the centrifugal force was high enough to push the particle through the interface. In the case shown in FIG. 14, upon visual inspection after each centrifuge run it can be seen that the particle 1220 has moved from the interface into the heavy phase 1202 and now sits at the bottom of the tube 1210. The minimum RPM required to transport the particle 1220 across the interface is used to calculate contact angle.

Figure 15:
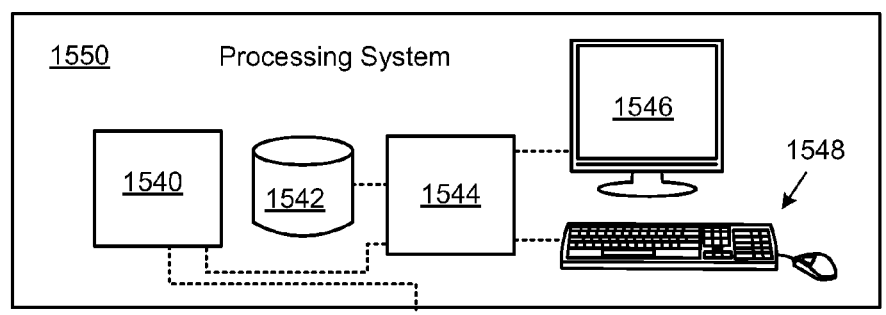
FIG. 15 is a schematic of a processing system used to run the computer code for the calculation of contact angle, according to some embodiments.

FIG. 15 is a schematic of a processing system used to run the computer code for the calculation of contact angle, according to some embodiments. Processing system 1550 includes one or more central processing units 1544, storage system 1542, communications and input/output modules 1540, a user display 1546 and a user input system 1548.

Figure 16:
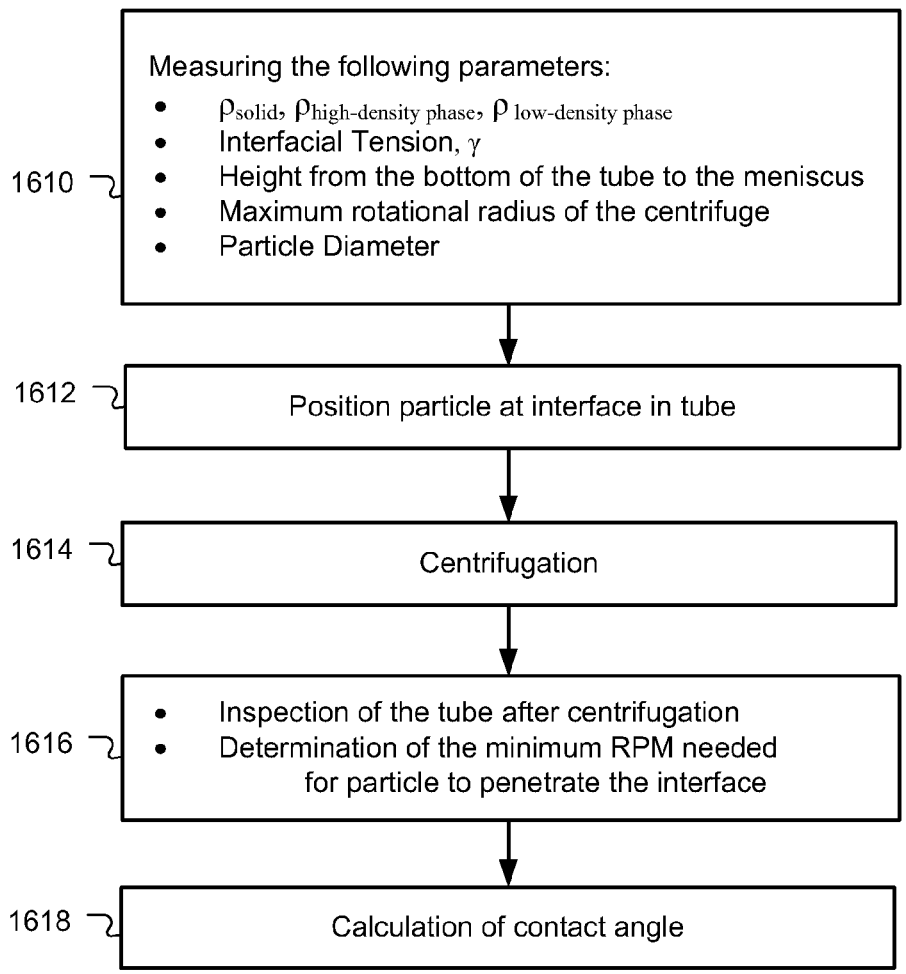
FIG. 16 is a flow chart showing certain steps in calculating a contact angle for a particle at an interface, according to some embodiments.

FIG. 16 is a flow chart showing certain steps in calculating a contact angle for a particle at an interface, according to some embodiments. In step 1610, one or more of the various parameters are measured or determined from other means: (1) the densities of the solid particle, the heavier liquid phase and the lighter liquid phase; (2) the interfacial tension, $\gamma$, such as using an apparatus as shown in FIG. 11; (3) the height from the bottom of the tube to the meniscus; (4) the maximum rotational radius of the centrifuge; and (5) the particle diameter. In step 1612, the particle is positioned at the interface in the tube, as shown in FIG. 12. In step 1614, the centrifuge is run, such as using a benchtop centrifuge as shown in FIG. 13. In step 1616, the tube is inspected after the centrifugation, and the minimum RPM needed for the particle to penetrate the interface is determined, such as described with respect to FIG. 14. In step 1618, a calculation is made to determine the contact angle, using a processing system such as shown in FIG. 15.

Figure 17:
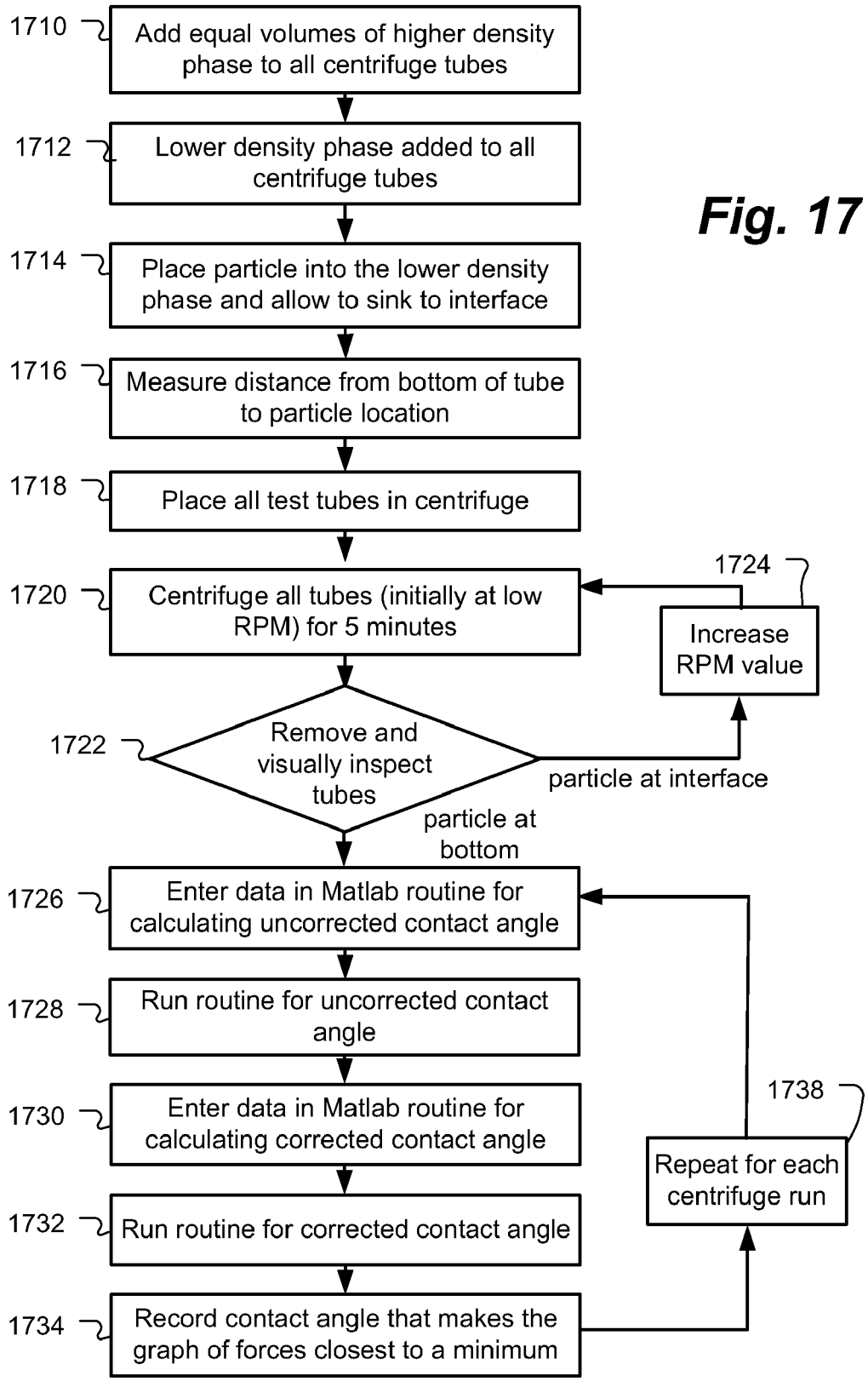
FIG. 17 is a flow chart showing steps involved in a centrifugation separation experiment, according to some embodiments.

FIG. 17 is a flow chart showing steps involved in a centrifugation separation experiment, according to some embodiments. In this experiment, a single chemical additive concentration was being evaluated. In step 1710, equal volumes of the higher density phase were added to all of the centrifuge tubes. The higher density phase in this experiment was deionised water with chemical additives added at known concentrations. For this experiment, only one concentration of chemical additive was being tested so there were numerous reproducibility runs. According to other embodiments, different concentrations of a chemical additive are added, and/or different compositions of chemical additives are added. In step 1712, with the test tube tilted slowly the lower density phase was added to all the centrifuge tubes. This produced a clean interface with no mixing of the two phases. The lower density phase in this experiment was oil. In step 1714, a hydrophobic particle was placed into the lower density phase and allowed to sink to the interface where it came to stop. In step 1716, the distance from the bottom of the centrifuge tube to the location of the particle at the interface was measured and recorded. In step 1718, all the centrifuge tubes were placed in the centrifuge that had been equipped with a swing out rotor. In step 1720, starting at a very low RPM, all the tubes were centrifuged for 5 minutes. The acceleration and deceleration of the centrifuge were set on the lowest settings. In step 1722, at the end of the centrifuge run, all the centrifuge tubes were removed and visually inspected to determine if the particle at the interface had penetrated the interface and sunk into the higher density phase. In step 1724, the RPM setting was increased slightly and centrifuge operated again for five minutes. At the end of each consecutive centrifuge run, all of the centrifuge tubes were removed and visually inspected to determine if the particle at the interface had penetrated the interface and sunk into the higher density phase. The steps of 1720 and 1724 were repeated until the particles in all the experiments had penetrated the interface and sunk in to the higher density phase. The minimum RPM needed for the each experiment to make the particle penetrate the interface was recorded.

Two Matlab routines were used to make calculations, examples of which are included herein, called "Calculate_Contact_Angle.m" and "Corrected_Contact_Angle.m" In step 1726, Calculate_Contact_Angle.m was opened and the values were added for solid density, higher density phase density, lower density phase density, minimum RPM needed for particle penetration, particle diameter, height from the bottom of the centrifuge tube to the meniscus, interfacial tension between the lower density and the higher density phase, and the maximum rotational radius of the centrifuge for the experimental run. Note that in this experiment, each run only accounted for one centrifuge tube. In step 1728, Calculate_Contact_Angle.m was run.

The only outputs of the program are a graph showing the forces are at a minimum and a value called "Uncorrected_Contact_Angle". This value was recorded. In step 1730, the routine Corrected_Contact_Angle.m was opened the values were entered for solid density, higher density phase density, lower density phase density, minimum RPM needed for particle penetration, particle diameter, height form the bottom of the centrifuge tube to the meniscus, interfacial tension between the higher density and the higher density phase, and the maximum rotational radius of the centrifuge. For the variable of Contact_Angle, enter the value recorded in Step 1728. In step 1732, the Corrected_Contact_Angle.m routine is run. The only output from this M-File is a graph showing that the forces are no longer at the minimum. The Corrected_Contact_Angle.m routine was opened again and the value of the Contact_Angle was slightly changed the program was run again. This should be repeated until the graph has been manually changed so the forces are very close to a minimum. In step 1734, the value for Contact_Angle that makes the graph of the forces closest to a minimum was recorded. In step 1738, the Matlab steps were repeated for all centrifuges runs.

Figure 18:
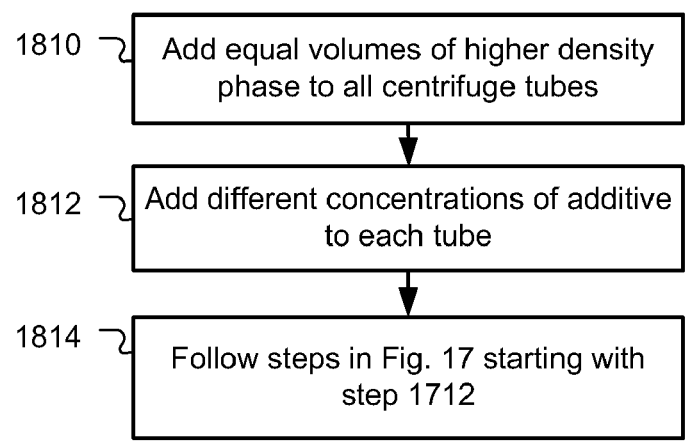
FIG. 18 is a flowchart showing steps involved in a centrifugation separation experiment evaluating multiple chemical additive concentrations, according to some embodiments.

FIG. 18 is a flowchart showing steps involved in a centrifugation separation experiment evaluating multiple chemical additive concentrations, according to some embodiments. In step, 1810, equal volumes of the higher density phase were added to all of the centrifuge tubes. The higher density phase is typically deionised water with chemical additives added at known concentrations. For this experiment multiple chemical additive concentrations and/or multiple chemical additives were tested. Therefore, in step 1812, in each centrifuge tube a different concentration was added. This provides parallel screening of numerous chemical additives or chemical additive concentrations. In step 1814, the steps of FIG. 17 were repeated beginning with step 1712. Thus, according to some embodiments, a screening technique is provided using sets of surfactant solutions with monotonically increasing concentrations. The concentrations could include zero. At a given centrifugal or gravitational acceleration a series sedimentation experiment is performed either simultaneously or sequentially. The concentration of surfactant solution is determined, which separates the breakthrough cases from the non-breakthrough ones.

FIG. 19 is a table showing experimental results, according to some embodiments. In this experiment, the minimum g force needed to transport the particle from the oil/water interface into the oil phase was found using a centrifuge. The interfacial tension was also found experimentally using a common pendant drop technique.

Using an analytical model, where the interface was characterized with one curvature only, an approximate contact angle, $\beta_{Calculated}$, was calculated. Because the single curvature is an approximation of the real surface having two curvatures, some deviations need to be corrected. Using a numerical model, which assumes the particle is spherical, the $\beta_{Calculated}$ is used as an initial guess and the graph of the forces acting on the particle versus the particle displacement is analyzed. If the g force found in the experiment is the minimum g force needed to transfer the particle into the oil phase the graph of the forces acting on the particle versus the particle displacement should also be at a minimum. The $\beta_{Calculated}$ will not yield a perfect minimum so it should be manually altered until the graph of the forces acting on the particle versus the particle displacement is at a minimum. Once a minimum is reached this value of contact angle is most accurate mathematically and is denoted as $\beta_{Corrected}$ in the table 1910 of FIG. 19.

Using flat surfaces of nearly identical composition and pre-treatment as the particle the contact angle was measured of a water droplet on the surface while in an oil environment. All variables (light phase, heavy phase, composition, pre-treatment, temperature etc.) were kept constant for the centrifugal separation experiments and the direct contact angle measurement using the slides. 95% confidence intervals for the measured contact angle are also reported.

It can be seen from the data in table 1910 that there is definite agreement between the mathematically calculated $\beta_{Corrected}$ and the direct measurement, $\beta_{Measured}$.

Although many embodiments have been described herein wherein an external force is applied to solid particle at the interface of two fluid phases using a centrifuge, according to other embodiments, other external forces can be used. For example, gravity can be used as the external force. According to some embodiments, gravity separation experiments are performed to find out at approximately which chemical additive concentration the microsphere would penetrate the oil/water interface with only gravity acting on it. In each of the test tubes the chemical additive concentration are systematically increased as multiples of its critical micellization concentration (CMC). A particle, which rests at the oil/water interface when no chemical additive is present, is introduced into the system. It is observed whether the particle sinks into the water-surfactant phase or rests at the interface for the increasing concentration of the chemical additive being investigated. Mathematically, $G=g=9.81$ m/s$^2$ (gravity acceleration) in this case. Additionally, although many embodiments have been described with a less dense fluid phase on "top" of a more dense phase, those of skill in the art will understand that other configurations are possible, such as two fluids side-by-side, depending on the properties of the fluid, the manner of applying external forces, and/or the configuration of the equipment used.

Although many embodiments have been described herein with respect to analysis of reservoir fluids such as oil and water, the present invention is also applicable to the analysis of many other types of fluids. According to some embodiments analysis with respect to one or more types of biomedical fluids is provided including but not limited to bodily fluids such as blood, urine, serum, mucus, and saliva. According to other embodiments, analysis with respect to one or more solids and fluids is provided in relation to environmental monitoring, including by not limited to water purification, water quality, and waste water processing, and potable water and/or sea water processing and/or analysis. According to yet other embodiments, analysis with respect to other solid and fluid chemical compositions is provided.

Whereas many alterations and modifications of the present invention will no doubt become apparent to a person of ordinary skill in the art after having read the foregoing description, it is to be understood that the particular embodiments shown and described by way of illustration are in no way intended to be considered limiting. Further, the invention has been described with reference to particular preferred embodiments, but variations within the spirit and scope of the invention will occur to those skilled in the art. It is noted that the foregoing examples have been provided merely for the purpose of explanation and are in no way to be construed as limiting of the present invention. While the present invention has been described with reference to exemplary embodiments, it is understood that the words, which have been used herein, are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

Following is a computer program listing of matlab routines "Calcluate_Contact_Angle.m" and "Corrected_Contact_Angle.m," according to some embodiments:

```
Calculate_Contact_Angle.m
% Calculate Contact angle
clear;
%
%The values enclosed in %%% must be filled in by the scientist.
%%%
ros=2476; %Solid Density (i.e. particle density)
rob=997; % higher density Phase Density (i.e. water phase containing
chemical additive)
roa=848; %Lower Density Phase Density (i.e. the oil phase)
RPM=780; %Minimum rotations per minute needed in the centrifuge to
make the particle penetrate the interface)
D=482.6; % Particle Diameter
H=6.5; %Height from bottom of the centrifuge tube to the meniscus (cm).
sigm=51.04e-3; % oil/water interface energy
R_Centrifuge=13.5; %The maximum rotational radius of the centrifuge in
cm.
%%%
%
%
R=(D/2)*10^-6; % particle radius, m
G=11.18*(R_Centrifuge-H)*(RPM/1000)^2;
g=((G*9.81)^2+9.81^2)^0.5;
N=300;
dfi=pi/N;
fi(1)=0;
for i=2:N+1;
        fi(i)=fi(i-1)+dfi;
end
% Dihotomy method
%*************************************************************
%
KG=100;
des=1e-9;
jok=0;
amin=0.0001;
amax=pi;
alf=0.5*(amin+amax);
for j=1:KG
for i=1:N+1;
dzet=(rob-roa)*g/sigm;
tet=fi(i);
if tet<=alf
        h2(i)=0;
    else
        h2(i)=sqrt(2*(1-cos(tet-alf))/dzet); % height of a meniscus
end
%
% Fource due to surface tension
%
Ft(i)=sigm*2*pi*R*sin(tet)*sin(tet-alf);
%
% Gravity and buyoance total force
%
Fb(i)=(ros-roa)*(4/3)*pi*R^3*g-(rob-roa)*g*pi*R^3*(2/3-
cos(tet)+cos(tet)^3/3)-(rob-roa)*g*pi*R^2*sin(tet)^2*h2(i);
%
Fs(i)=Fb(i)-Ft(i);
%
    if Fs(i)<=0
            jok=1;
            break;
    end
end
        if jok==0
        if min(Fs)<=des
            break
        else
            amax=alf;
        end
            elseif jok==1
            amin=alf;
            jok=0;
            end
        alf=0.5*(amin+amax);
end
plot(fi,Fs);
xlabel('Displacement (m)');
ylabel('Total Force Acting on the Particle (N)');
title('Force VS Displacement');
alf=alf*180/pi;
Uncorrected_Contact_Angle=180-alf
```

```
Corrected_Contact_Angle.m
% Spherical Particle Passing through Liquid-Liquid Boundary
clear;
%
%The values enclosed in %%% must be filled in by the scientist.
%%%
ros=2476; %Solid Density (i.e. particle density)
rob=997; % higher density Phase Density (i.e. water phase containing
chemical additive)
roa=848; % Lower Density Phase Density (i.e. the oil phase)
RPM=780; %Minimum rotations per minute needed in the centrifuge to
make the particle penetrate the interface)
D=482.6; % Particle Diameter
H=6.5; %Height from bottom of the centrifuge tube to the meniscus in cm.
sigm=51.04e-3; % oil/water interface energy
R_Centrifuge=13.5; %The maximum rotational radius of the centrifuge in
cm.
Contact_Angle=91.00; %Contact angle found using
Calculate_Contact_Angle.m is
the initial guess but it is varied so the output graph is at a minimum.
%%%
%
%
alf=180-Contact_Angle; % Contact angle, degrees
alf=pi*alf/180 ; % Contact angle, radians
R=(D/2)*10^-6; % particle radius, m
G=11.18*(R_Centrifuge-H)*(RPM/1000)^2;
g=((G*9.81)^2+9.81^2)^0.5;
N=100;
ur=0;
dz=2*R/N;
z(1)=0;
dx=R/400;
dx=dx/R; % normalization
mur=8000;
for i=2:N+1;
        z(i)=z(i-1)+dz;
        if z(i)<-R
            x0(i)=sqrt(R^2-z(i)^2);
```

-continued

```
    x0(i)=x0(i)/R; % normalization
      else
    x0(i)=sqrt(R^2-(z(i)-R)^2);
    x0(i)=x0(i)/R; % normalization
      end
end
        for i=1:N+1
dzet=-(rob-roa)*g/sigm;
dzet=dzet*R^2; % Normalization
tet(i)=acos(1-z(i)/R);
        end
        %
        %
        for i=1:N+1
if tet(i)<=alf
        h2(i)=0;
else
    % Calculation of the meniscus thickness
% Modified Euler Method;
%x(1)=x0(i);
zt(1)=tan(tet(i)-alf);
dvar;
%[dv,it]=min(pyt);
if ur==1
  %   h2(i)=h2(i-1);
  %   Fs(i)=Fs(i-1);
    for j=1:ik-2
    h2u(j)=h2(j);
    Fsu(j)=Fs(j);
    zu(j)=z(j);
    end
    break
end
h2(i)=h2g*R;
    %h2=sqrt(2*(1-cos(tet-alf))/dzet); % height of a meniscus
end
%
% Fource due to surface tension
%
Ft(i)=sigm*2*pi*R*sin(tet(i))*sin(tet(i)-alf);
%
% Gravity and buyoance total force
%
Fb(i)=(ros-roa)*(4/3)*pi*R^3*g-(rob-roa)*g*pi*R^3*(2/3-
cos(tet(i))+cos(tet(i))^3/3)-(rob-roa)*g*pi*R^2*sin(tet(i))^2*h2(i);
%Fb(i)=(ros-roa)*(4/3)*pi*R^3*g-(rob-roa)*g*(pi*R^3*(2/3-
cos(tet(i))+cos(tet(i))^3/3)+pi*R^2*sin(tet(i))^2*h2(i));
%
Fs(i)=Fb(i)-Ft(i);
        end
        if ur==1
plot(zu,Fsu);
        else
plot(z,Fs) ;
        end
xlabel('Displacement (m)');
ylabel('Total Force Acting on the Particle (N)');
title('Displacement VS Force');
```

What is claimed is:

1. A method for determining a property of a solid material relating to wettability comprising:
   positioning a solid material at an interface between a first fluid phase and a second fluid phase, the second fluid phase being denser than the first fluid phase;
   applying an external force to the solid material so as to urge the solid material towards the second fluid phase;
   determining whether the solid material passes through the interface phase due to the external force; and
   calculating a parameter of the solid material relating to wettability based in part on whether the solid material has passed through the interface and the density of the second fluid phase.

2. A method according to claim 1 wherein the parameter of the solid material relating to wettability is a contact angle.

3. A method according to claim 2 further comprising calculation a value for wettability of the solid material based in part on the calculated contact angle.

4. A method according to claim 1 wherein the parameter of the solid material relating to wettability is capillary pressure.

5. A method according to claim 1 wherein the calculating of the parameter relating to wettability is based in part on the density of the first phase.

6. A method according to claim 1 wherein the calculating of the parameter relating to wettability is based at least in part on parameters relating to the following: density of the first phase, density of the second phase, density of the solid material, amount of the external force applied, size of the solid material, and interfacial tension between the first phase and the second phase.

7. A method according to claim 1 wherein the calculating of the parameter relating to wettability includes accounting for at least two curvatures representing the interface between the first phase and the second phase as deformed by the solid material.

8. A method according to claim 1 wherein the first or second phase includes a chemical additive and the method further comprises evaluating the chemical additive based in part on whether the solid material passes through the interface due to the external force.

9. A method according to claim 1 further comprising:
   positioning a plurality of pieces of the solid material in a plurality of containers each containing the first and second phases, wherein at least one of the pieces of the solid material being positioned at an interface between the first and second phases in each of the plurality of containers, and wherein the external force is simultaneously applied to each of the pieces of solid material; and
   determining for each of the containers whether one or more of the pieces of the solid material passes through the interface due to the external force.

10. A method according to claim 1 wherein the external force is gravity.

11. A method according to claim 1 wherein the external force is centrifugal force generated by a centrifuge.

12. A method according to claim 1 wherein the first fluid phase is an organic solution and the second fluid phase is an aqueous solution.

13. A method according to claim 12 wherein the first fluid phase is crude oil and the solid material is a piece of reservoir rock.

14. A method according to claim 1 wherein the first fluid phase is a gas and the second fluid phase is an aqueous solution.

15. A method according to claim 1 wherein the first fluid phase is a gas and the second fluid phase is an organic solution.

16. A method according to claim 1 wherein the external force is applied repeatedly at increasing amounts and following each application of the external force the determination of whether the solid material passes through the interface is repeated.

17. A method for evaluating a chemical additive comprising:
   positioning a solid material at an interface between the first fluid phase containing the additive and a second fluid phase, the second fluid phase being denser than the first fluid phase, wherein the first phase or the second phase contains the chemical additive to be evaluated;
   applying an external force to the solid material so as to urge the solid material towards the second fluid phase;
   determining whether the solid material passes through the interface due to the external force; and
   evaluating the chemical additive based at least in part on whether the solid material passes through the interface.

18. A method according to claim 17 wherein the second phase includes the chemical additive.

19. A method according to claim 18 wherein the additive is a surfactant.

20. A method according to claim 18 wherein the evaluation of the chemical additive is based in part on the density of the first phase.

21. A method according to claim 17 wherein the evaluation of the chemical additive is based at least in part on parameters relating to the following: density of the first phase, density of the second phase, density of the solid material, amount of the external force applied, size of the solid material, and interfacial tension between the first phase and the second phase.

22. A method according to claim 17 wherein the evaluation of the chemical additive includes accounting for at least two curvatures representing the interface between the first phase and the second phase as deformed by the solid material.

23. A method according to claim 17 wherein the external force is gravity.

24. A method according to claim 17 wherein the external force is centrifugal force generated by a centrifuge.

25. A method according to claim 17 further comprising:
positioning a plurality of pieces of the solid material in a plurality of containers each containing the first and second phases, wherein at least one of the pieces of the solid material being positioned at an interface between the first and second phases in each of the plurality of containers, and wherein the external force is simultaneously applied to each of the pieces of solid material; and
determining for each of the containers whether one or more of the pieces of the solid material passes through the interface due to the external force.

26. A method according to claim 25 wherein the second phase in each container contains different amounts of the chemical additive.

27. A method according to claim 25 wherein the second phase in each container contains a different composition of chemical additive.

28. A method according to claim 17 wherein the external force is applied repeatedly at increasing amounts and following each application of the external force the determination of whether the solid material passes through the interface is repeated.

29. A method according to claim 17 wherein the first fluid phase is an organic solution and the second fluid phase is an aqueous solution.

30. A method according to claim 29 wherein the first fluid phase is crude oil and the solid material is a piece of reservoir rock.

31. A method according to claim 17 wherein the first fluid phase is a gas and the second fluid phase is an aqueous solution.

32. A method according to claim 17 wherein the first fluid phase is a gas and the second fluid phase is an organic solution.

33. A system for determining a property of a solid material relating to wettability comprising:
a first container for including a first fluid phase, a second fluid phase and a solid material positioned at an interface between the first and second phases, the second fluid phase being denser than the first fluid phase;
an apparatus adapted to accept the first container so as to apply an external force to the solid material so as to urge the solid material towards the second fluid phase; and
a processing system adapted and programmed to calculate a parameter of the solid material relating to wettability based in part on whether the solid material has passes through the interface due to the application of the external force.

34. A system according to claim 33 wherein the parameter of the solid material relating to wettability is a contact angle.

35. A system according to claim 34 wherein the processing system is further adapted and programmed to calculate a value for wettability of the solid material based in part on the calculated contact angle.

36. A system according to claim 33 wherein the calculation of the parameter relating to wettability is based in part on the density of the first phase.

37. A system according to claim 33 wherein the calculation of the parameter relating to wettability is based at least in part on parameters relating to the following: density of the first phase, density of the second phase, density of the solid material, amount of the external force applied, size of the solid material, and interfacial tension between the first phase and the second phase.

38. A system according to claim 33 wherein the calculation of the parameter relating to wettability includes accounting for at least two curvatures representing the interface between the first phase and the second phase as deformed by the solid material.

39. A system according to claim 33 wherein the apparatus is a centrifuge.

40. A system according to claim 33 further comprising a plurality of containers for including the first and second phases with pieces of the solid material positioned at an interface between the first and second phases, wherein the apparatus is adapted to accept the plurality of containers so as to apply an external force to each piece of solid material.

41. A system for evaluating a chemical additive comprising:
a first container for including a first fluid phase, a second fluid phase and a solid material positioned at an interface between the first and second phases, the second fluid phase being denser than the first fluid phase and the first or second phase containing the chemical additive to be evaluated; and
an apparatus adapted to accept the first container so as to apply an external force to the solid material so as to urge the solid material towards the second fluid phase, such that an evaluation can be made of the chemical additive based at least in part on whether the solid material passes through the interface.

42. A system according to claim 41 wherein the second phase includes the chemical additive and the additive is a surfactant.

43. A system according to claim 41 wherein the evaluation of the chemical additive is based in part on the density of the first phase.

44. A system according to claim 41 wherein the evaluation of the chemical additive includes accounting for at least two curvatures representing the interface between the first phase and the second phase as deformed by the solid material.

45. A system according to claim 41 wherein the apparatus is a centrifuge.

46. A system according to claim 41 further comprising a plurality of containers for including the first and second phases with pieces of the solid material positioned at an interface between the first and second phases, wherein the apparatus is adapted to accept the plurality of containers so as to apply an external force to each piece of solid material.

* * * * *